(12) United States Patent
Chitre et al.

(10) Patent No.: US 7,174,220 B1
(45) Date of Patent: Feb. 6, 2007

(54) CONSTRUCTION OF A MEDICAL ELECTRICAL LEAD

(75) Inventors: Yougandh Chitre, Valencia, CA (US); John R. Helland, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 156 days.

(21) Appl. No.: 10/802,462

(22) Filed: Mar. 16, 2004

(51) Int. Cl. *A61N 1/00* (2006.01)

(52) U.S. Cl. ........................ 607/119; 600/374

(58) Field of Classification Search ........ 607/115–133, 607/373–377
See application file for complete search history.

(56) References Cited

U.S. PATENT DOCUMENTS

| | | | |
|---|---|---|---|
| 4,559,951 A | 12/1985 | Dahl et al. ................... | 128/642 |
| 4,840,186 A | 6/1989 | Lekholm et al. ............. | 128/784 |
| 4,945,342 A * | 7/1990 | Steinemann ............ | 174/113 R |
| 5,796,044 A * | 8/1998 | Cobian et al. ............... | 174/103 |
| 6,141,576 A * | 10/2000 | Littmann et al. ........... | 600/381 |
| 6,934,589 B2 * | 8/2005 | Sundquist et al. .......... | 607/122 |
| 2002/0055764 A1 * | 5/2002 | Malonek et al. ............ | 607/122 |
| 2003/0050681 A1 * | 3/2003 | Pianca et al. ............... | 607/125 |
| 2003/0220677 A1 * | 11/2003 | Doan et al. .................. | 607/122 |

FOREIGN PATENT DOCUMENTS

WO    WO02/094334 A1    11/2002

\* cited by examiner

*Primary Examiner*—Mark Bockelman

(57) ABSTRACT

An implantable cardiac stimulation lead system for use with an implantable stimulation device includes at least a pair of conductors, braided together and extending between proximal and distal ends and co-extruded with flexible resilient insulation material. Each conductor may be a multi-strand cable composed of MP35N or DFT and have its outer peripheral surfaces coated with insulative material. An electrical connector is coupled to the proximal end of the lead system for connection with a stimulation device and includes terminals electrically connected to the conductors. The proximal connector is thereby electrically coupled to a distal tip electrode and to at least one electrode proximally spaced from the distal tip electrode. The lead system may include an elongated tubular lead body of flexible resilient insulative material having a longitudinally extending lumen for receiving a stylet for aid in implanting the lead system. Alternatively, an introducer sheath may be employed for implantation.

14 Claims, 9 Drawing Sheets

CONSTRUCTION OF A MEDICAL ELECTRICAL LEAD

FIELD OF THE INVENTION

The present invention relates generally to implantable medical devices for providing stimulating pulses to selected body tissue, for example, the heart, and more particularly, to the lead assemblies connecting such devices with the tissue to be stimulated.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers or defibrillators for providing precisely controlled stimulation pulses to the heart. However, the appended claims are not intended to be limited to any specific example or embodiment described herein.

Pacemaker leads form the electrical connection between the cardiac stimulator and the heart tissue which is to be stimulated. As is well known, the leads connecting such cardiac stimulators with the heart may be used for pacing, for sensing electrical signals produced by the heart, for defibrillation, or for a combination of those procedures in which case a single lead serves as a bidirectional pulse transmission link between the stimulator and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, maybe coiled, conductor or plurality of conductors surrounded by an insulating tube or sheath typically couples the connector pin at the proximal end and the electrodes at or near the distal end.

The implantable cardiac stimulation leads with which the present invention is concerned may take the form, for example, of pace-makers capable of pacing and sensing in at least one chamber of the heart. Indeed, the present invention, may relate to a programmable dual chamber pacemaker wherein the basic configuration of the pacemaker, e.g. unipolar or bipolar, can be changed, including the grounding configuration and ground potentials used within the pacemaker.

Generally, a heart stimulator uses one or two flexible leads having one end connected to itself and the other end connected to electrodes placed in close proximity to the heart. These leads are used to stimulate or pace the heart. Also, these leads are used to sense the heart activity by picking up electrical signals from the heart.

In order to properly pace or sense or defibrillate, the cardiac stimulator device has to be able to deliver a stimulating pulse to the heart or to sense an electrical signal from the heart, and this requires that there be an electrical return path. If, within a given heart chamber, a unipolar lead is used containing a single conductor and the return path is the conductive body tissue and fluids. The return path is connected to the stimulator device by connecting the stimulator device's electrical common or ground to the stimulator's metal enclosure, typically referred to as the case or housing. The case or housing, in turn, makes contact with the body tissue and/or fluids.

An alternative solution to using a unipolar lead in a given heart chamber is to use a double lead/electrode in the heart chamber, known as a bipolar lead. In a bipolar lead, a second conductor is spiraled over and insulated from a first conductor along the length of the lead. At the distal end of the lead, one of the conductors is connected to a first electrode, referred to as the "tip" electrode, and the second conductor is connected to a second electrode, referred to as a "ring" electrode. The ring electrode is generally situated about 10 to 20 mm proximally from the tip electrode. The tip electrode is typically placed in contact with heart tissue, while the ring electrode is in electrical contact with the blood, and in some instances can also be making contact with heart tissue. Because body and heart tissue and fluids are conductive, the ring electrode of a bipolar lead, in contact with the body fluids or tissue, serves as an electrical return for both pacing and sensing.

As indicated, pacing or sensing using the pacer case or enclosure as part of the electrical return path is known as unipolar pacing or sensing. Pacing or sensing using the lead ring electrode and associated lead conductor as the electrical return path is known as bipolar pacing or sensing. There are numerous factors to consider when deciding whether unipolar or bipolar pacing and/or sensing should be used. Bipolar pacing has, in general, the advantage of requiring slightly less energy than unipolar pacing, and with regard to sensing, bipolar pacing impedance is usually greater than unipolar impedance. Further, bipolar sensing is less prone to far-field signals, crosstalk, and myopotential sensing than is unipolar sensing since its dipole is so much smaller. Crosstalk generally refers to a pacer mistakenly sensing a heart activity in one heart chamber immediately after the other chamber is paced. Bipolar sensing reduces crosstalk resulting from a pacing stimulus in the opposite chamber. Bipolar pacing is preferred if pectoral or diaphragmatic stimulation occurs.

Present day cardiac stimulation leads are required to have multiple conductors serving multiple electrodes. Each of the conductors is housed in lumina formed in the extruded insulation material. The insulation material may be composed of either silicone or polyurethane, or a combination thereof. Advances in technology have given rise to added complexity in the manufacture of pacing and defibrillation leads. Future designs of leads warrant simplicity in construction. This in turn gives rise to reduced touch time associated with the construction of leads and a reduction in costs associated from reduced steps of construction. Furthermore, over the past few years, there has been a substantial effort to reduce the diameter of endocardial pacing and defibrillation leads. The size of a lead body can facilitate placement of multiple leads through a single blood vessel and also minimize interference between the lead body and the tricuspid valve (applicable for leads implanted in the right ventricle or RV). Indeed, the ability to accommodate two leads in an 8 F introducer would be a remarkable advance. Indeed, this is the goal sought be the present invention.

Typical of the known prior art is U.S. Pat. No. 4,840,186 to Lekholm et al. In this instance, an implantable lead has conductors wound in a multi-pole helix. The conductors are individually insulated by a first insulating material and the insulated conductors are embedded in, and axially separated from each other by a second tube-formed insulating material. The inner opening of the tube receives a helically wound stylet guide coil which may also be a multi-pole conductor arrangement. The conductors may be helically wound, multi-filament wires. Preferably, according to the disclosure, all helically wound arrangements in the lead are wound in the same direction so that the lead is still when rotating it in one direction and flexible when rotating it the other way.

Another instance of the prior art is found in U.S. Pat. No. 4,559,951 to Dahl et al. Here, a catheter assembly designed for long term or short term implantation in an animal body includes a flexible tube of a biocompatible polymeric material in which plural electrical conductors are helically wound at a predetermined pitch with the conductors being laterally offset from one another and totally buried between the walls of the tube whereby many conductive signal paths can be established through the catheter without increasing its overall diameter. According to that disclosure, the inclusion of the helically wound conductors in the walls of the tube also allow the torque transfer, flexibility and structural properties to be tailored to fit a variety of applications. Such a catheter may be used as a cardiac pacer lead assembly or as an instrument for carrying out various diagnostic catheterization procedures.

It was in light of the foregoing that the present invention was conceived and has now been reduced to practice.

SUMMARY

An implantable cardiac stimulation lead system for use with an implantable stimulation device includes at least a pair of conductors, braided together and extending between proximal and distal ends and co-extruded with flexible resilient insulation material. Each conductor may be a multistrand cable composed of MP35N, titanium alloy, drawn filled tube (DFT), and the like and have its outer peripheral surfaces coated with insulative material. An electrical connector is coupled to the proximal end of the lead system for connection with a stimulation device and includes terminals electrically connected to the conductors. The proximal connector is thereby electrically coupled to a distal tip electrode and to at least one electrode proximally spaced from the distal tip electrode. The lead system may include an elongated tubular lead body of flexible resilient insulative material having a longitudinally extending lumen for receiving a stylet for aid in implanting the lead system. Alternatively, an introducer sheath may be employed for implantation.

One embodiment includes co-extruding conductors, preferably coated cables, with the insulation matrix, either silicone or polyurethane or combination of those materials. The advantages that this methodology offers over traditional configurations of cable conductor leads include:

(1) current leads utilize an insulation tubing furbished with lumina. Construction of the lead entails having to string the cables through the lumina along the length of the entire lead. This often poses problems resulting in kinking of the cables. The procedure just described places restrictions on the size of the lumina. To allow ease of stringing of the cable conductors and to account for lot to lot variation, a certain clearance is allowed between the cables and the walls of the lumen. This in turn could allow for the cables to move around within the lumen space, which could result in "internal abrasion" This is especially a concern if the cable conductors are not coated, for example, with a fluoropolymer.

Further advantages will become apparent by comparing the current manner of assembly of a lead with that being proposed. The proposed assembly process employing a lead configuration as taught in this disclosure results in a significant reduction of the process steps.

This reduction of steps translates to a reduction in cycle time and would thereby result in either allowing operators to work on alternate tasks in the saved time or enabling manufacture of a larger number of units can be produced in the same amount of time.

In another embodiment, the cables are braided thereby reducing the overall size of the lead.

In still another embodiment, the tubing assembly is furbished with a lumen for the passage of a stylet, as opposed to the well-known catheter-delivery approach.

Further features, advantages, and benefits will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENTS

Figure 1:
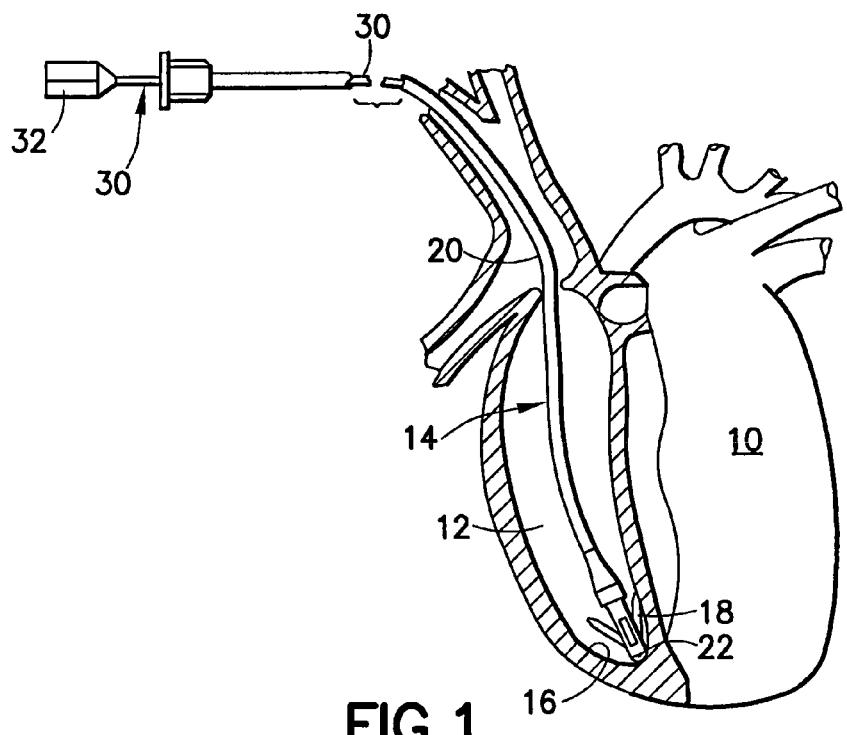
FIG. 1 is a perspective view illustrating a heart with a portion cut away to reveal an implantable lead assembly, which may embody the present invention, secured therein to a wall of the heart.

Refer now to the drawings and, initially, to FIG. 1 which illustrates a diagrammatic perspective view, partially cut away and shown in section, of a heart 10 into the right ventricle 12 of which is inserted a body implantable lead 14 of the endocardial type incorporating features of the present invention. Although the present invention will be described with reference to the embodiments shown in the drawings, it should be understood that the present invention can be embodied in many alternate forms or embodiments. In addition, any suitable size, shape or type of elements or materials could be used. The lead 14 is attached to an interior wall 16 of the heart 10 by means of fixing tines 18, for example, which engage the tissue or trabeculae of the heart.

Figure 2:
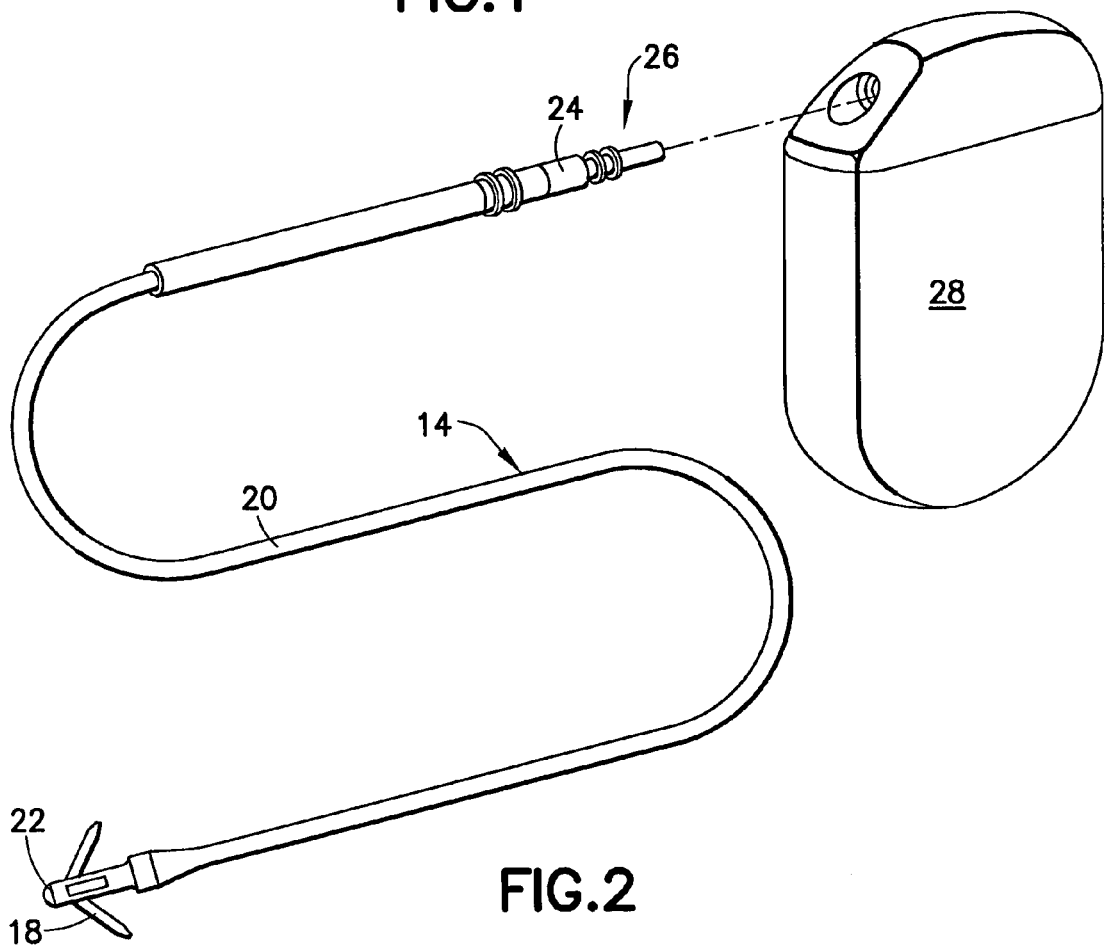
FIG. 2 is a perspective view of an implantable lead which may embody the invention in combination with a stimulating device such as a pacemaker.

As further illustrated, the lead 14 also includes an insulating sheath 20 interconnecting a distal electrode 22 secured adjacent the interior wall 16 and an electrical connector 24 (see FIG. 2) at a proximal end 26 to which can be attached a source of electrical energy such as a pacemaker 28 In FIG. 1, a stylet 30 is illustrated inserted within the insulating sheath 20 with the aid of a manipulating device 32 and may be used to provide rigidity to the lead 14 during insertion of the lead into the heart 10.

Figure 3:
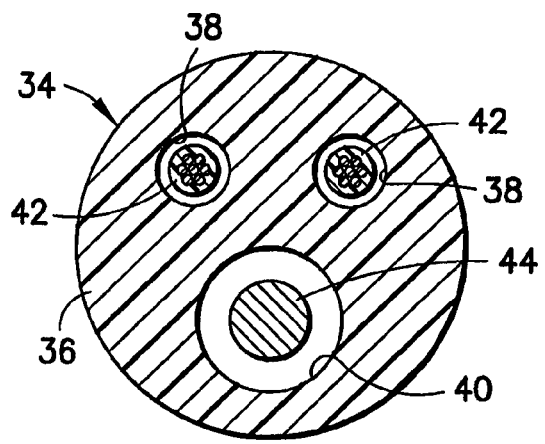
FIG. 3 is a cross section view of a known lead construction.
Figure 4:
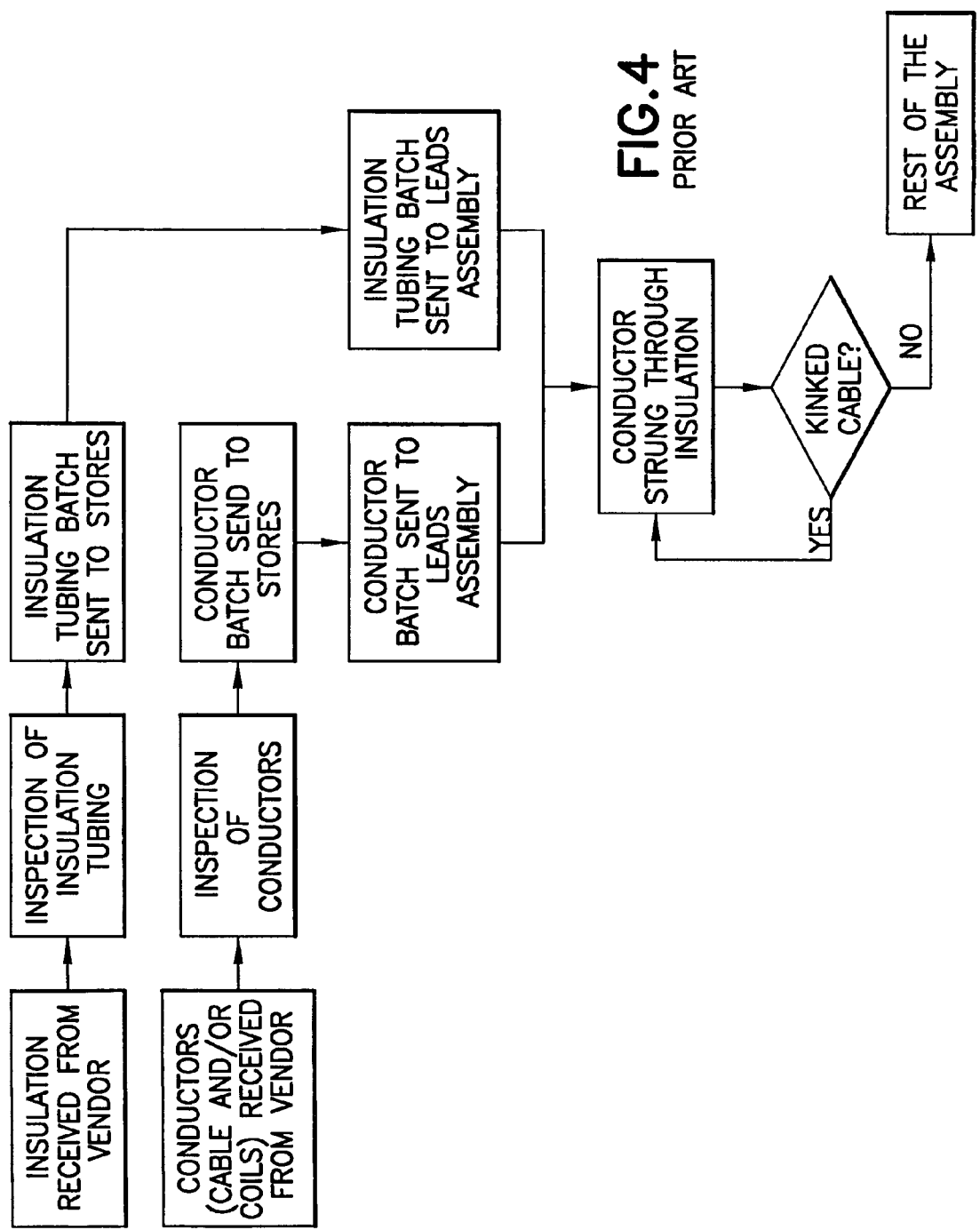
FIG. 4 is a flow diagram to relate the manufacture of a known type of lead.

Turning now to FIG. 3, it was earlier explained that current leads such as lead 34 utilize an insulative tubing 36 furbished with lumina 38, 40. Construction of the known lead 34 entails having to string conductors 42 through the lumina 38 along the length of the entire lead. The lumen 40 may serve to receive a stylet 44 in the known manner for implanting the lead 34. This construction unfortunately often poses problems resulting in kinking of the conductors 42 as they are introduced through the lumina 38. A flow diagram depicting the manufacturing process for the known lead is presented in FIG. 4.

Figure 5:
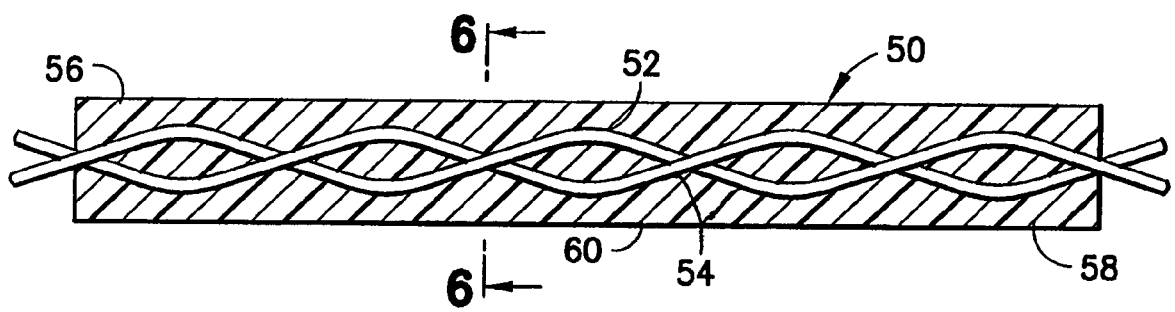
FIG. 5 is a longitudinal elevation view, in section, illustrating one embodiment of the invention.
Figure 6:
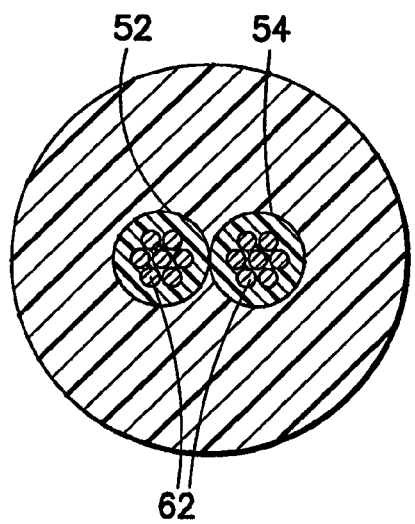
FIG. 6 is a cross section view generally taken along line 6—6 in FIG. 5.

According to the invention as illustrated in FIGS. 5 and 6, an implantable cardiac stimulation lead system 50 is provided for use with an implantable stimulation device 28, for example, as seen in FIG. 1. The lead system 50 includes a pair of conductors 52, 54, braided together and extending between proximal and distal ends 56, 58, respectively, and co-extruded with flexible resilient insulation material 60, preferably silicone or polyurethane or a combination of those materials.

Each conductor is typically a multi-strand cable which may variously be of a 1×5, 1×7, 1×19 construction composed of MP35N or of DFT, or other configuration of a plurality of strands, e.g. 5 strands. Individual strands are indicated by reference numeral 62. The outer peripheral surfaces of the conductors 52, 54 are coated with insulative material, preferably a fluoropolymer such as PTFE or ETFE.

Figure 7:
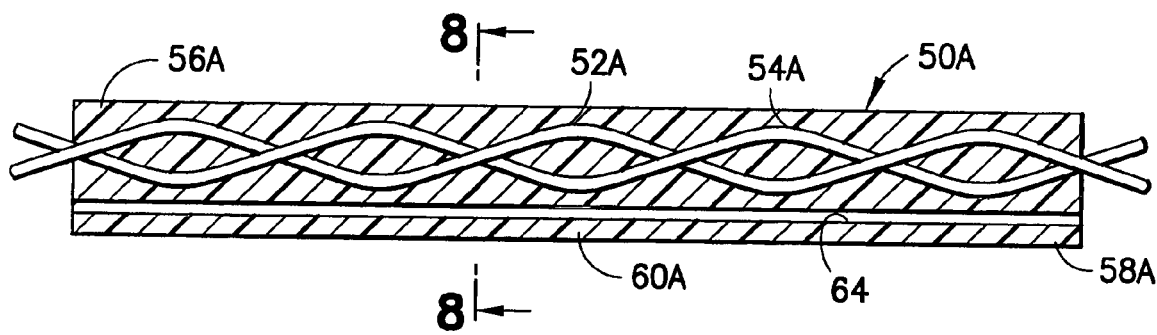
FIG. 7 is a longitudinal elevation view, in section, illustrating another embodiment of the invention.
Figure 8:
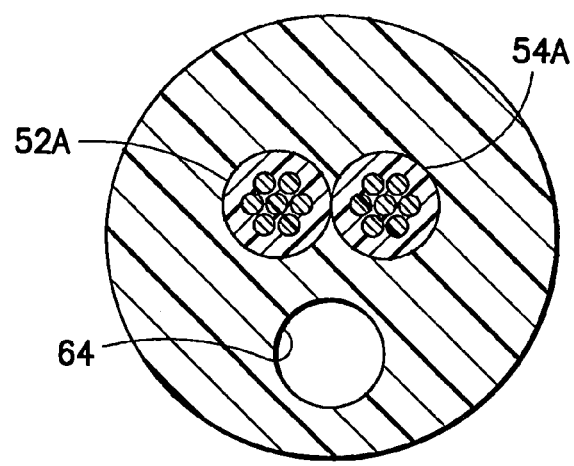
FIG. 8 is a cross section view generally taken along line 8—8 in FIG. 7.

In FIGS. 7 and 8, a slightly different version of the invention is illustrated. In this instance, an implantable cardiac stimulation lead system 50A includes a pair of conductors 52A, 54A, braided together and extending between proximal and distal ends 56A, 58A, respectively, and co-extruded with flexible resilient insulation material 60A as earlier described. Again, each conductor is typically a multi-strand cable composed of the earlier mentioned materials and similarly coated with insulative material. In this instance, the elongated tubular lead body of flexible resilient insulative material 60A has a lumen 64 extending longitudinally between the proximal and distal ends for reception of a stylet for aid in implanting the lead system. In one embodiment, a stylet with a lubricious coating can be used. The insulative material 60A may be a combination of silicone and polyurethane, a polycarbonate, or any suitable chemical composition as is well known to those skilled in the art.

Figure 9:
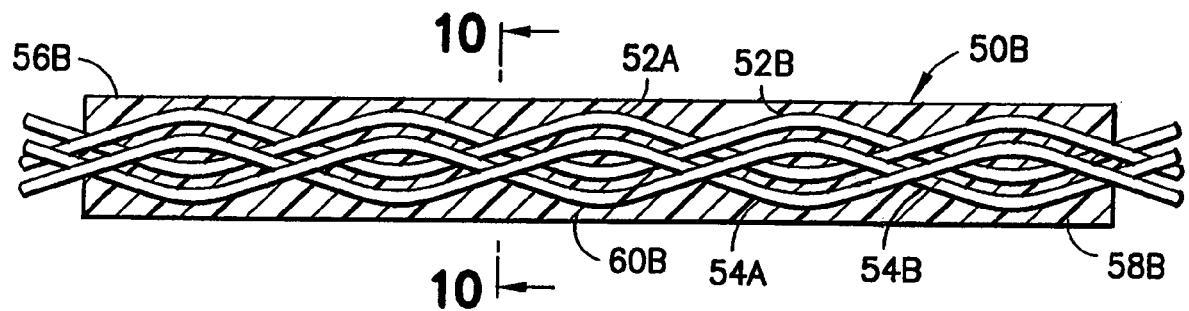
FIG. 9 is a longitudinal elevation view, in section, illustrating yet another embodiment of the invention.
Figure 10:
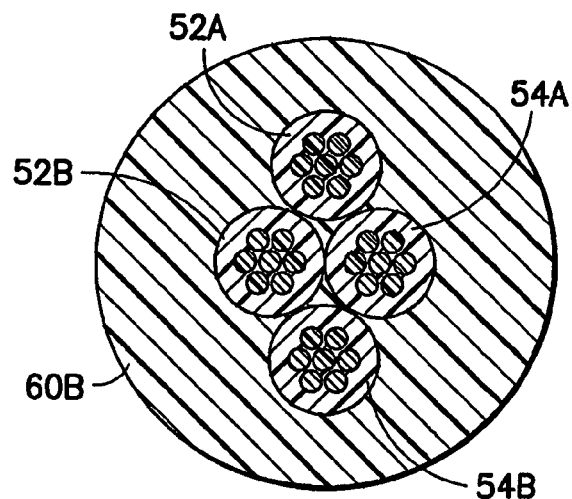
FIG. 10 is a cross section view generally taken along line 10—10 in FIG. 9.

In FIGS. 9 and 10, yet another a slightly different version of the invention is illustrated. In this instance, an implantable cardiac stimulation lead system 50B includes a plurality of conductors 52A, 52B, 54A, 54B all braided together and extending between proximal and distal ends 56B, 58B, respectively, and co-extruded with flexible resilient insulation material 60B as earlier described. Again, each conductor is typically a multi-strand cable composed of the earlier mentioned materials and similarly coated with insulative material.

Figure 11:
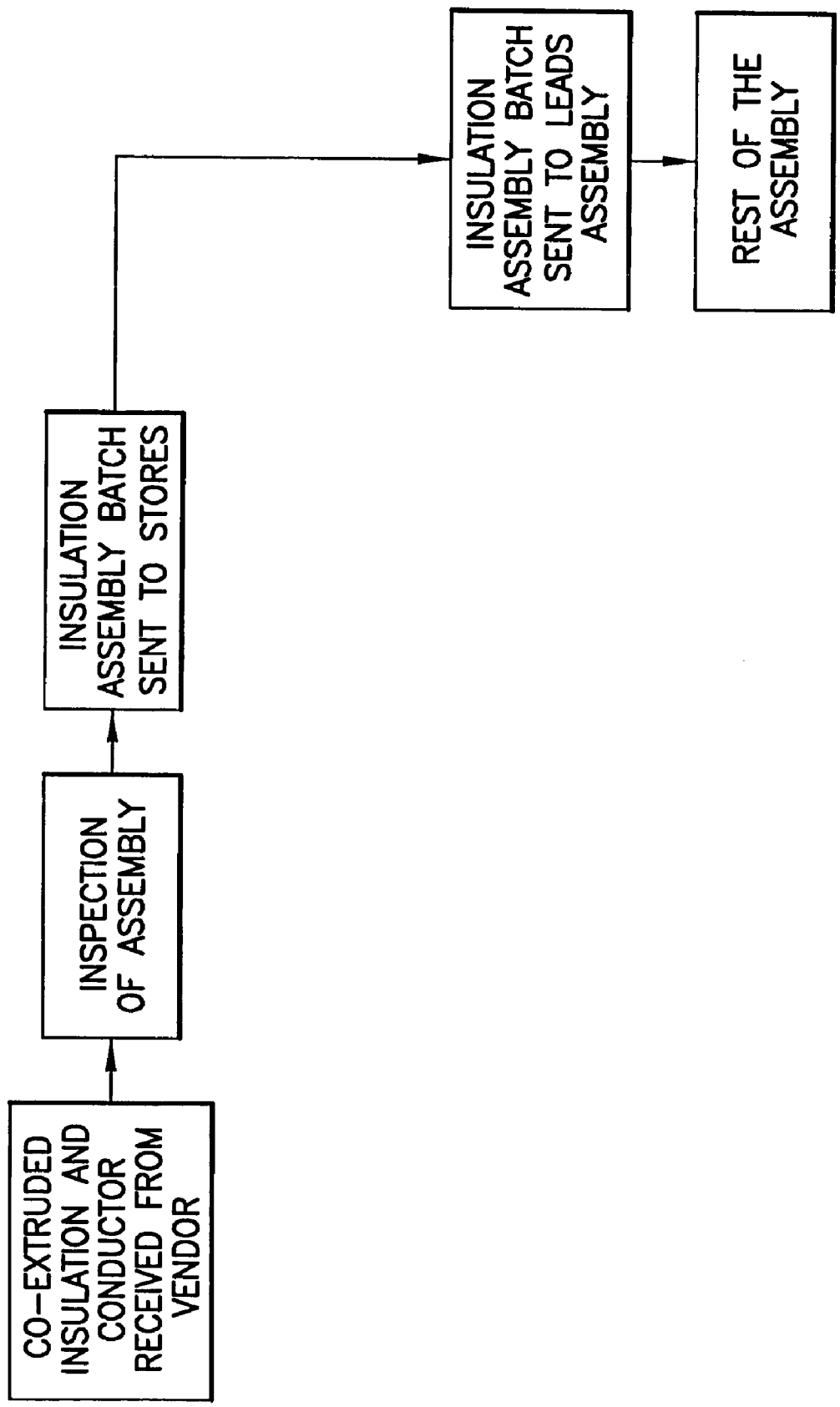
FIG. 11 is a flow diagram to relate the manufacture of a type of lead embodying the invention.

A flow diagram depicting the manufacturing process for the lead system of the invention is presented in FIG. 11.

Figure 12:
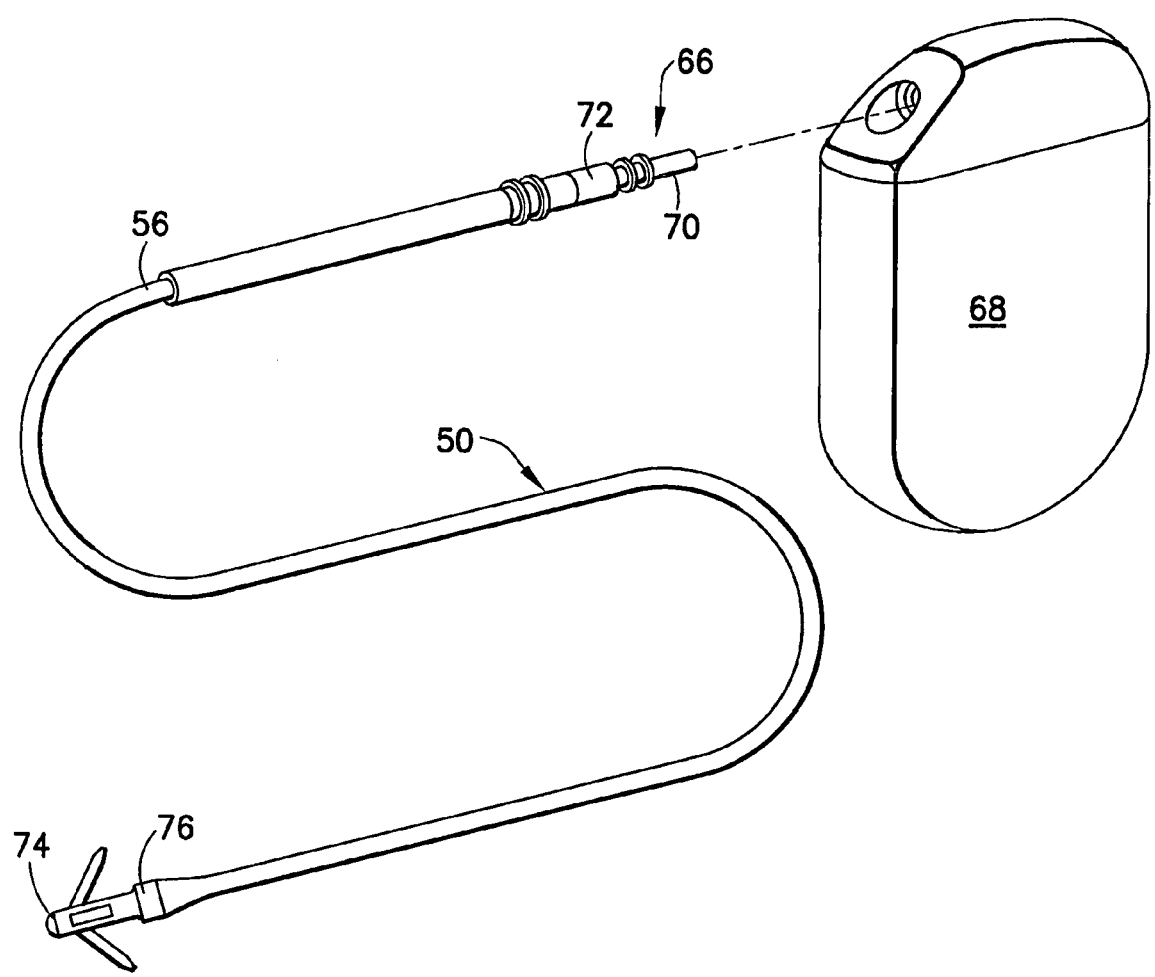
FIG. 12 is a perspective view of an implantable lead embodying one instance of the invention in combination with a stimulating device such as a pacemaker.

In FIG. 12, the lead system 50 is illustrated in combination with an electrical connector 66 and a stimulation device 68. The electrical connector 66 is coupled to the proximal end 56 of the lead system 50 for connection with the stimulation device 68 and includes two terminals 70, 72 electrically connected to respective ones of the conductors 52, 54. Operating through the conductor 52, the terminal 70 is connected to a distal tip electrode 74. In a similar fashion, operating through the conductor 54, the terminal 72 is connected to an electrode 76 proximally spaced from the distal tip electrode and shown as a ring electrode.

Figure 13:
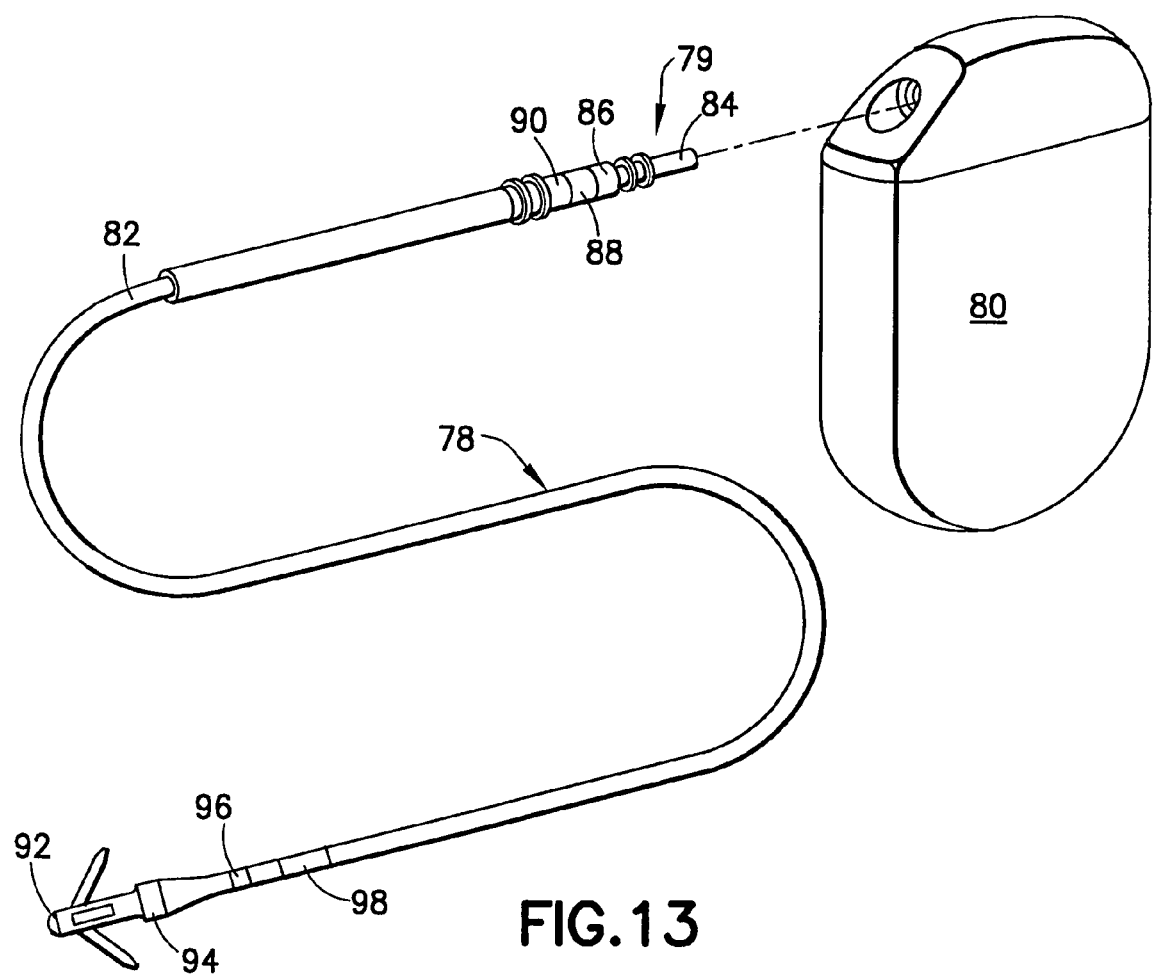
FIG. 13 is a perspective view of an implantable lead embodying another instance of the invention in combination with a stimulating device such as a pacemaker.

In FIG. 13, a lead system 78 is illustrated in combination with an electrical connector 79 and a stimulation device 80. In a manner as earlier described, the electrical connector 79 is coupled to a proximal end 82 of the lead system 78 for connection with the stimulation device 80 and includes four terminals 84, 86, 88, and 90, in this exemplary instance, electrically connected to respective ones of conductors not shown but generally as earlier described. Operating through one conductor, the terminal 84 is connected to a distal tip electrode 92. In a similar fashion, operating through another conductor, the terminal 86 is connected to a ring electrode 94 proximally spaced from the distal tip electrode for bi-polar pacing. Additionally, operating through still another conductor, the terminal 88 is connected to another electrode 96 also proximally spaced from the distal tip electrode for sensing. Finally, for purposes of this description, the terminal 90 is connected to yet another electrode 98 also proximally spaced from the distal tip electrode for defibrillation. In this instance, as in the previous embodiments, the plurality of conductors is braided together and they extend between the proximal and distal ends of the lead system 78 and are co-extruded with flexible resilient insulation material as earlier described.

Figure 14:
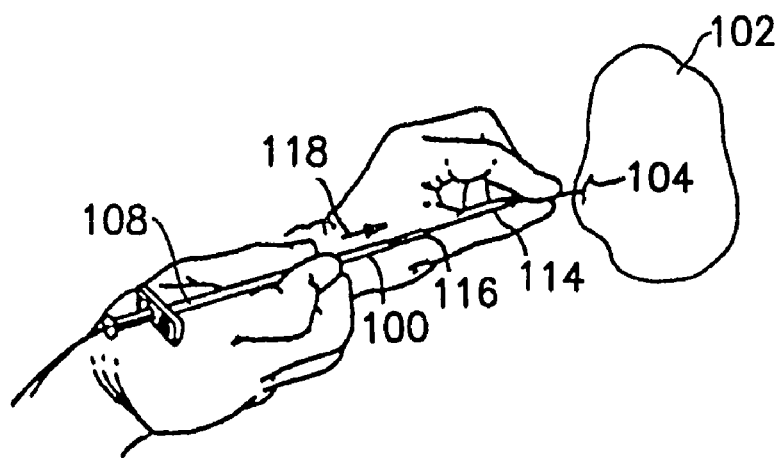
FIG. 14 is a perspective view depicting a procedure of using an introducer sheath for the implantation of a transvenous endocardial lead.
Figure 15:
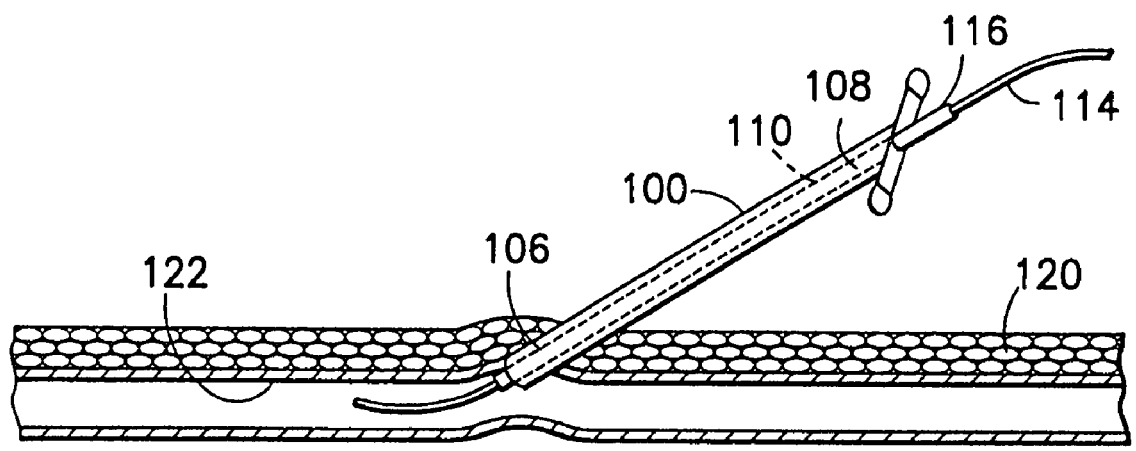
FIG. 15 is an elevation view, partly in cross section, continuing with depiction of the procedure of using an introducer sheath for the implantation of a transvenous endocardial lead.

With the embodiment of FIG. 13 or with any of the earlier-described embodiments, an elongated introducer sheath 100 may be used as seen in FIGS. 14 and 15 to introduce the lead system into a body 102 through a small skin incision 104. Having a first end 106 configured for insertion within a body and a second end 108 extending out of the body, the introducer sheath has a central lumen 110 configured to permit the introduction of the lead system into the body.

The small skin incision 104 is made at an entry site for a guide wire 114. The introducer sheath 100, together with a tapered vessel dilator 116, as an assembly, is threaded onto a proximal end of the guide wire 114. The introducer sheath 100 and vessel dilator 116 are advanced in the direction of an arrow 118, through the subclavian fascia 120 and into the subclavian vein 122, until a short length (e.g., 2 to 8-cm) of the introducer sheath 100 and vessel dilator 116 remain exposed along with the wire guide 114, as shown in FIG. 15.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. An implantable cardiac stimulation lead system for use with an implantable stimulation device, the lead system comprising:
   at least a pair of conductors, braided together and extending between proximal and distal ends and co-extruded with flexible resilient insulation material to form a lead body;
   wherein each of the conductors comprises:
   a solid core having multi-strand cable; and
   an outer peripheral surface coated with insulative material;
   an electrical connector coupled to the proximal end of the lead system for connection with a stimulation device and further comprising at least two terminals electrically connected to respective ones of the at least two conductors;
   a distal tip electrode; and
   at least one electrode proximally spaced from the distal tip electrode;
   a first of the pair of conductors connecting the proximal connector and the distal tip electrode;
   a second of the pair of conductors connecting the proximal connector and the electrode proximally spaced from the distal tip electrode.

2. The lead system of claim 1:
   wherein each conductor is a multi-strand cable composed of at least one of MP35N and titanium alloy.

3. The lead system of claim 1:
   wherein each conductor is a multi-strand cable composed of DFT.

4. The lead system of claim 1:
   wherein the insulative material is a fluoropolymer.

5. The lead system of claim 1:
   wherein the insulative material is PTFE.

6. The lead system of claim 1:
   wherein the insulative material is ETFE.

7. The lead system of claim 1:
   wherein the electrode proximally spaced from the distal tip electrode is a ring electrode.

8. The lead system of claim 1 and further comprising:
   an elongated tubular lead body of flexible resilient insulative material having a lumen extending longitudinally between a proximal end at the proximal connector and a distal end at the distal tip electrode for selective reception of a stylet for aid in implanting the lead system.

9. The lead system of claim 8:
   wherein the flexible resilient insulation material is silicone.

10. The lead system of claim 8:
    wherein the flexible resilient insulation material is polyurethane.

11. The lead system of claim 8:
    wherein the flexible resilient insulation material is a combination of silicone and polyurethane.

12. An implantable cardiac stimulation lead system for use with an implantable stimulation device, the lead system comprising:
    a plurality of conductors, braided together and extending between proximal and distal ends and co-extruded with flexible resilient insulation material to form a lead body;
    wherein each of the conductors comprises:
    a solid core having multi-strand cable; and
    an outer peripheral surface coated with insulative material;
    an electrical connector coupled to the proximal end of the lead system for connection with a stimulation device and further comprising a plurality of terminals electrically connected to respective ones of the plurality of conductors;
    a distal tip electrode;
    a plurality of electrodes proximally spaced from the distal tip electrode;
    one of the plurality of conductors connecting the proximal connector and the distal tip electrode; and
    others of the plurality of conductors connecting the proximal connector and, respectively, each of the plurality of electrodes proximally spaced from the distal tip electrode.

13. The lead system of claim 12:
    wherein the plurality of electrodes proximally spaced from the distal tip electrode includes at least one type of pacing, sensing, and defibrillation electrodes.

14. The lead system of claim 12 and further comprising:
    an elongated introducer sheath having a first end configured for insertion within a body and a second end extending out of the body, the introducer sheath having a central lumen configured to permit the introduction of the lead system into the body.

* * * * *